United States Patent
Mazuir

(10) Patent No.: US 7,480,366 B2
(45) Date of Patent: Jan. 20, 2009

(54) OPTIMIZING THE QUANTITY OF X-RAYS RECEIVED BY A PATIENT IN A DENTAL X-RAY IMAGE ACQUISITION SYSTEM

(75) Inventor: Alain Mazuir, Saint Maximim Sainte Baume (FR)

(73) Assignee: Sopro, La Ciotat Cedex (FR)

( * ) Notice: Subject to any disclaimer, the term of this patent is extended or adjusted under 35 U.S.C. 154(b) by 0 days.

(21) Appl. No.: 11/882,774

(22) Filed: Aug. 6, 2007

(65) Prior Publication Data
US 2007/0269002 A1    Nov. 22, 2007

(51) Int. Cl.
*H05G 1/54* (2006.01)
(52) U.S. Cl. .............................. 378/117; 378/91; 378/38
(58) Field of Classification Search .................. 378/91, 378/96, 97, 101–118, 98.8, 38
See application file for complete search history.

(56) References Cited

U.S. PATENT DOCUMENTS

| | | | |
|---|---|---|---|
| 4,082,953 A | 4/1978 | Krause et al. | |
| 4,618,974 A | 10/1986 | Grassme et al. | |
| 5,058,147 A | 10/1991 | Nishikawa et al. | |
| 5,331,166 A | 7/1994 | Yamamoto et al. | |
| 5,631,943 A | 5/1997 | Miles | |
| 5,694,448 A | 12/1997 | Morcom | |
| 6,345,215 B1 * | 2/2002 | Drechsler | 700/306 |
| 6,404,854 B1 * | 6/2002 | Carroll et al. | 378/98.8 |

* cited by examiner

*Primary Examiner*—Jurie Yun
(74) *Attorney, Agent, or Firm*—Clark & Brody

(57) ABSTRACT

This system for dental X-ray image acquisition comprises an X-ray generator and a control module for controlling an intra-oral sensor. The module includes means for sending a command to the generator in application of at least one predetermined criterion for preventing, stopping, or modifying the power of X-ray emission. The use of this system for optimizing the quantity of X-rays received by a patient.

13 Claims, 1 Drawing Sheet

OPTIMIZING THE QUANTITY OF X-RAYS RECEIVED BY A PATIENT IN A DENTAL X-RAY IMAGE ACQUISITION SYSTEM

BACKGROUND OF THE INVENTION

The present invention relates to a dental X-ray image acquisition system, to an X-ray generator, and to a command module for controlling an intra-oral sensor suitable for use in such a system.

In known manner, a dental X-ray image acquisition system mainly comprises an X-ray generator and an intra-oral sensor that is sensitive to said X-rays, and that is associated with a command module for acquiring the X-ray image.

The X-ray generator is required to be fitted with control means, generally a button, enabling the operator to trigger the emission of X-rays in manual and deliberate manner.

Such an X-ray generator is also fitted with a timer enabling the operator to set a predetermined duration for X-ray emission, it being understood that the operator can also voluntarily stop the emission of X-rays by using the above-mentioned control means.

In a first known system, the starting and the end of acquisition by the sensor are under the control of the generator.

In another known system, in particular as described in U.S. Pat. No. 5,331,166, X-ray sensitive pellets are integrated in the intra-oral sensor, said pellets being adapted to send a signal to the command module of the sensor which controls the starting and the stopping of digital image acquisition as a function of the intensity of said signal.

Also known, in particular from the disclosure of U.S. Pat. No. 5,694,448, is an imaging system in which the output level from a charge-coupled device (CCD) sensor is continuously monitored so as to detect when the generator is emitting X-rays, i.e. whenever said level becomes greater than a noise level. When such emission is detected, image acquisition proper is performed.

Given that the CCD sensor is read and emptied continuously in cyclical manner, in order to make a comparison with the noise level, a most unfavorable circumstance can arise during which no image is acquired even though X-rays have begun to be emitted by the generator.

In practice, 10% to 20% of the X-rays emitted by the generator can be lost in this way, and that is naturally harmful to the patient.

To sum up, none of the above-mentioned prior art systems is capable of optimizing the quantity of X-rays received by the patient since the practitioner can adjust the timer in intuitive manner only. In practice, practitioners prefer to use an overdose of X-rays in order to be sure of obtaining an image of good quality.

OBJECT AND SUMMARY OF THE INVENTION

A main object of the present invention is thus to mitigate those drawbacks by proposing a dental X-ray image acquisition system comprising:
  an X-ray generator comprising means for triggering the emission of X-rays, a timer enabling an operator to set a predetermined duration for X-ray emission, and means for automatically stopping the emission at the end of the predetermined duration; and
  an intra-oral sensor responsive to X-rays, associated with a sensor command module, and adapted to acquire the image during said emission. In the system:
  the module comprises means for sending a command in application of at least one predetermined criterion to the generator to prevent, stop, or modify the power of X-ray emission before the end of the predetermined duration so as to control the quantity of X-rays emitted by the generator; and
  the generator includes means for receiving the stop command, the means for stopping the generator being adapted to prevent, stop, or modify the power of the emission on receiving the command.

Thus, in accordance with the invention, X-rays are emitted by the generator only while the digital image is being integrated by the intra-oral sensor.

The invention also provides an X-ray generator and an intra-oral sensor command module suitable for use in such a system.

In accordance with the invention, the module possesses mean for interrupting or preventing X-ray emission in application of predetermined criterion as explained below.

Naturally, when none of the criteria is satisfied, then the emission of X-rays is interrupted by the generator at the end of the predetermined duration as set by the operator. It should be observed that such a generator complies with regulations that merely require that the emission of X-rays should stop automatically in a manner that is initially programmed by the operator.

Various conditions or criteria used by the command module for remotely interrupting or preventing the emission of X-rays by the generator are described below.

Naturally, these criteria are not exclusive of one another.

In a first embodiment, the module sends the command on detecting a malfunction of the intra-oral sensor.

In a second embodiment, the module possesses means for detecting the type of intra-oral sensor to which it is connected and means for determining the appropriate duration for X-ray emission as a function of the sensor type. The command is then sent to the generator at the end of said duration.

In a third embodiment, the command module determines the duration of X-ray emission as a function of the type of resolution desired for the X-ray image, and sends the command to the generator at the end of said duration.

In this embodiment, the command module may obtain the level of resolution from a remote device, e.g. a computer. Image resolution may also be programmed in the module itself.

In a fourth embodiment, the module includes means for measuring the mean gain of a sequence of previously acquired images, and means for determining a quantity of X-ray emission that is adjusted as a function of said mean gain and as a function of a predetermined desired gain. In this embodiment, the command is sent to the generator to modify the quantity of X-rays emitted by the generator in compliance with said adjusted quantity.

BRIEF DESCRIPTION OF THE DRAWING

Other characteristics and advantages of the present invention appear from the following description given with reference to accompanying FIG. 1 which shows an embodiment that is not limiting in any way.

Figure 1:
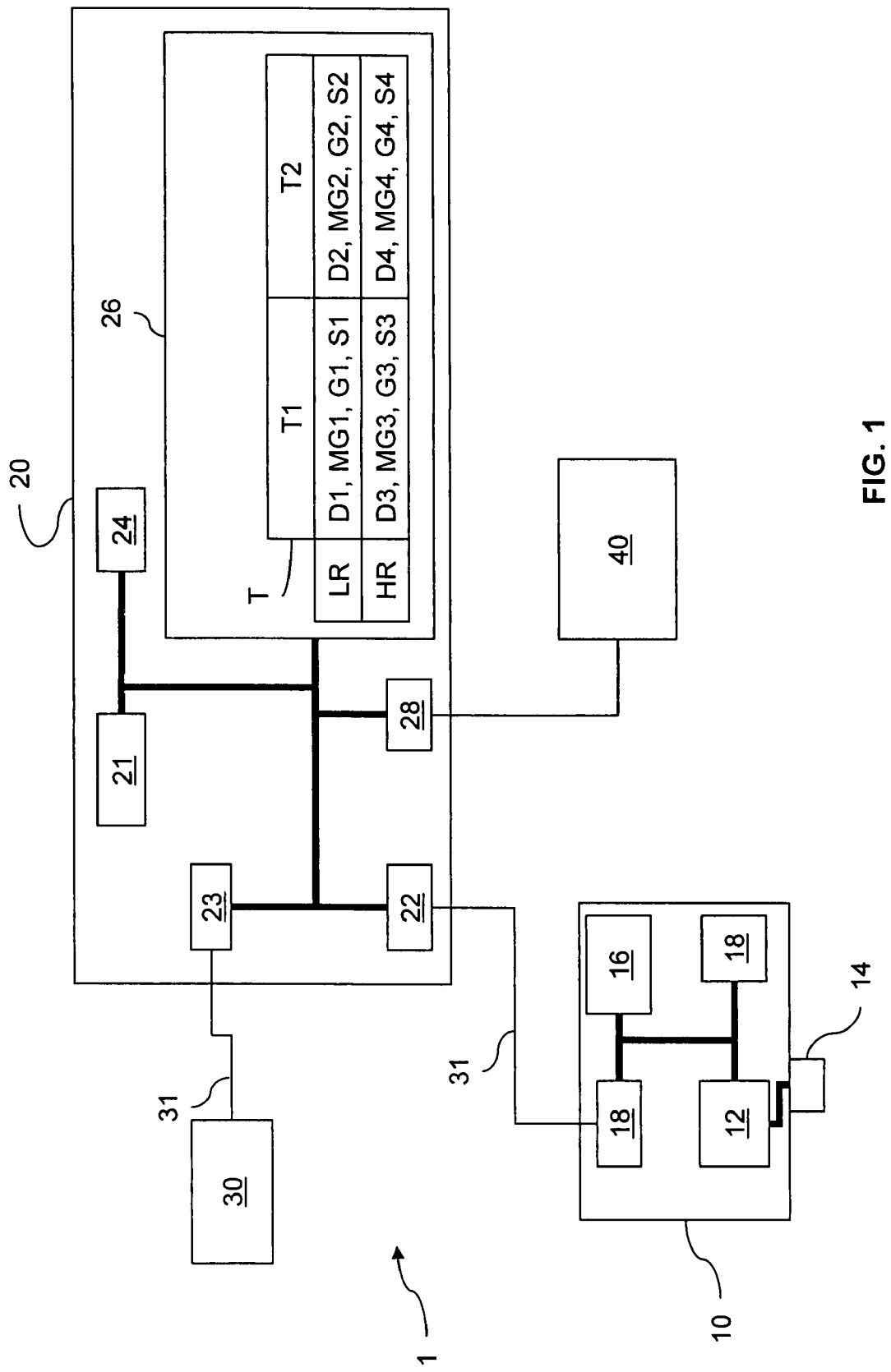
FIG. 1 is a diagram showing a dental X-ray image acquisition system 1 in accordance with the invention.

The system 1 includes an X-ray generator 10 in accordance with the invention in a preferred embodiment.

The X-ray generator 10 comprises an X-ray source 16 and means 14, e.g. a button, for manually triggering or stopping the emission of X-rays by the source 16.

The generator 10 also comprises a timer 18 enabling the operator to set a predetermined duration for the source 16 to emit X-rays.

The generator 10 also has means, e.g. a microprocessor 12 in combination with the timer 18, for causing the emission of X-rays to be stopped automatically at the end of the predetermined duration.

The acquisition system 1 also comprises an intra-oral sensor 30 that is sensitive to X-rays, e.g. of the complementary metal oxide semiconductor (CMOS) or CCD type.

The intra-oral sensor 30 is controlled by a control module 20 in accordance with the invention and is connected thereto by a wire 31.

Images acquired by the sensor 30 are also conveyed by the wire 31 for first processing in the module 20.

In the embodiment described herein, the module 20 is controlled by a microprocessor 21 adapted in particular to control the intra-oral sensor 30 and to receive digital image data coming from said intra-oral sensor via an inlet/outlet port 23.

In accordance with the invention, the generator 10 and the control module 20 have respective communications means 18, 22 serving in particular to enable the module 20 to send a command to the generator 10.

In a first variant embodiment, these communications means 18, 22 are means for wired communication.

In a variant, these communications means may be constituted by wireless communications means, for example complying with the Bluetooth standard.

On receiving such a command, the processor 12 of the generator 10 interrupts the emission of X-rays by the source 16, or modifies the quantity of X-rays being emitted.

If the command is received while the source 16 is inactive, the processor 12 prevents any subsequent emission of X-rays by said source 16 until the operator voluntarily takes manual action.

In the preferred embodiment described herein, the module 20 of the invention includes means 28 for communicating with an external system 40, e.g. constituted by a personal computer (PC) type computer.

The personal computer 40 may be used in particular for displaying the digital images acquired by the intra-oral sensor 30.

In the preferred embodiment described herein, the operator may also use the remote system 40 for selecting a level of resolution (low resolution LR, high resolution HR) of the X-ray images acquired by the sensor 30, with the resolution level LR, HR being received by the control module 20 via its communications interface 28.

In a variant (not shown) the resolution LR, HR can be programmed directly in the module 20.

In the preferred embodiment described herein, the processor 21 of the control module 20 is adapted to detect a malfunction of the intra-oral sensor 30, e.g. by reading a register of the inlet/outlet port 23 provided for this purpose.

On detecting a malfunction, the processor 21 sends the command to interrupt generating X-rays to the generator 10 via the communications means 22.

In the preferred embodiment described herein, the processor 21 is also adapted to determine the type (T1 or T2) of the intra-oral sensor 30, e.g. by reading a register provided for this purpose in the inlet/outlet port 23.

In the preferred embodiment described herein, the control module 30 has a non-volatile memory 26 in which there is stored a table T having as many columns as there are known types T1, T2 of sensor 30 that might be controlled by the module 20, and as many rows as there are possible resolutions LR, HR for the X-ray images acquired by the sensor.

In this example, the table T has two rows and two columns.

The table T stores four values for each pair (sensor type: T1, T2; and image resolution: HR, LR):

a duration Di for X-ray emission by the generator 10 for the corresponding type/resolution pair;

a mean gain MGi measured for a previously acquired image sequence corresponding to said type/resolution pair;

a desired gain Gi for the images acquired by said type/resolution pair; and a step size Si for adjusting the duration Di when the mean gain MGi is different from the desired gain Gi.

In the preferred embodiment described herein, for the first images acquired by an intra-oral sensor of a type Ti, with a resolution LR or HR, the processor 21 of the control module 20 reads the desired duration Di for X-ray emission from the table T.

The control module 20 includes means for detecting the beginning of X-ray emission by the generator 10.

Since these means do not form part of the invention, they are not described in detail herein. They may be constituted in particular by any of the prior art means mentioned in the introduction to this document, namely receiving an explicit command coming from generator 10, e.g. via the communications channel 31, or by detector means of the X-ray sensitive pellet type placed in the intra-oral sensor 30.

In any event, the processor 21 of the control module 20 is adapted to start a timer 24 for measuring the duration of X-ray emission from detection of the beginning of said emission.

When said measured duration is equal to the duration Di stored in the table T, the processor 21 sends the command to the X-ray generator 10 to cause the generator 10 to stop emitting X-rays.

As described above, for each acquired image, the processor 21 updates the mean gain MGi of an image sequence acquired by a sensor type Ti and resolution LR or HR pair.

Once a sufficient number of images have been acquired, when the mean gain MGi differs from the gain Gi desired for a particular type of image, the processor 21 adjusts the duration Ti with a step of size Si. For example, if the desired equilibrium gain Gi is 6 decibels (dB), and if the measured mean gain MGi for the latest images is a gain of 10 dB, then the processor 21 increases the emission duration Di by a step Si, e.g. of 5 milliseconds.

In a variant, the module 20 sends a command to the generator 20 so that for the next acquisition it modifies the quantity of X-rays emitted in accordance with said adjusted quantity. The person skilled in the art will understand that modifying the step size Si amounts to adjusting the power at which the generator emits X-rays for constant duration of emission.

What is claimed is:

1. A dental X-ray image acquisition system comprising:
   an X-ray generator comprising means for triggering the emission of X-rays, a timer enabling an operator to set a predetermined emission duration for said X-rays, and means for automatically stopping said emission at the end of said predetermined duration; and
   an intra-oral sensor sensitive to X-rays, associated with a command module for controlling said sensor, and adapted to acquire an image during said emission;
   said command module including means for starting said acquisition on detecting said triggering; wherein:
   said module includes means for receiving image acquisition data from the x-ray sensitive intra-oral sensor and means for generating a command for use by the generator, in application of at least one predetermined criterion related to the image acquisition data, to the generator to prevent, stop, or modify the emission power of said X-rays before the end of said predetermined duration, so as to control the quantity of X-rays emitted by the generator aiming in the acquisition of an image of good quality while not using an overdose of X-rays, and means for sending the command to the generator; and wherein said generator includes means for receiving said command, the means for stopping the generator being adapted to prevent, stop, or modify the power of said emission on receiving said command.

2. An acquisition system according to claim 1, wherein said module includes means for detecting a malfunction of said intra-oral sensor, and means for sending said command on detecting said malfunction.

3. An acquisition system according to claim 1, wherein said module includes means for determining the type of the Intra-oral sensor, means for determining an X-ray emission duration as a function of said type, means for measuring the duration of X-ray emission, and means for sending said command at the end of said duration in order to stop the emission of X-rays by the generator.

4. An acquisition system according to claim 1, wherein said module includes means for obtaining a level of resolution desired for said image, means for determining a duration for X-ray emission as a function of said level, means for measuring the duration of X-ray emission, and means for sending said command at the end of said duration in order to stop the emission of X-rays by the generator.

5. An acquisition system according to claim 4, wherein said means for obtaining the resolution level, are programming means of said module or means for receiving information representative of said level coming from a remote device.

6. An acquisition system according to claim 1, wherein said module includes means for measuring the mean gain of a sequence of at least one previously acquired image, means for determining a quantity of X-ray emission adjusted as a function of said mean gain and as a function of a predetermined desired gain, and means for sending said command in order to modify the quantity of X-rays emitted by said generator in compliance with said adjusted quantity.

7. An X-ray generator comprising
means for triggering the emission of X-rays,
a timer enabling an operator to adjust a predetermined duration for emission of said X-rays, and
means for stopping said emission at the end of said predetermined duration,
said generator including means for receiving a command coming from a command module of an intra-oral sensor sensitive to said rays that receives images acquisition data from the intra-oral sensor, said command being sent by the module in application of at least one predetermined criterion related to the image acquisition data, said stop means being adapted to prevent, stop, or modify said emission quantity on receiving said command.

8. A module for commanding an X-ray sensitive intra-oral sensor, the module comprising: means for receiving image acquisition data from the x-ray sensitive intra-oral sensor; means for generating a command for use by a generator of X-rays as a function of at least one predetermined criterion related to the image acquisition data, the command serving to prevent, stop, or modify the emission of said X-rays by the generator aiming in the acquisition of an image of good quality while not using an overdose of X-rays, and means for sending the command to the generator.

9. A module according to claim 8, including means for detecting a malfunction of said intra-oral sensor, and means for sending said command on detection of said malfunction.

10. A module according to claim 8, including means for detecting the type of the intra-oral sensor, means for determining a duration for X-ray emission as a function of said type, means for measuring the duration of X-ray emission, and means for sending said command at the end of said duration in order to stop the emission of X-rays by the generator.

11. A module according to claim 8, including means for obtaining a level of resolution desired for said image, means for determining a duration of X-ray emission as a function of said level, means for measuring the duration of X-ray emission, and for sending said command at the end of said duration to stop the emission of X-rays by the generator.

12. A module according to claim 11, wherein said means for obtaining the level of resolution are means for programming said module or means for receiving information representative of said level coming from a remote device.

13. A module according to claim 8, including means for measuring the mean gain of a sequence of at least one previously acquired image, means for determining a quantity of X-ray emission adjusted as a function of said mean gain and of a predetermined desired gain, and means for sending said command so as to modify the quantity of X-rays emitted by said generator in compliance with said adjusted quantity.

* * * * *

UNITED STATES PATENT AND TRADEMARK OFFICE
CERTIFICATE OF CORRECTION

| | |
|---|---|
| PATENT NO. | : 7,480,366 B2 |
| APPLICATION NO. | : 11/882774 |
| DATED | : January 20, 2009 |
| INVENTOR(S) | : Mazuir |

It is certified that error appears in the above-identified patent and that said Letters Patent is hereby corrected as shown below:

The following information should be listed on the front page of the patent:

RELATED U.S. APPLICATION DATA
Continuation of application No. PCT/FR06/00106, filed on Jan. 18, 2006

FOREIGN APPLICATION PRIORITY DATA
Feb. 9, 2005 (FR)...05/01290

Signed and Sealed this

Fifth Day of January, 2010

David J. Kappos
*Director of the United States Patent and Trademark Office*